United States Patent [19]

Freimark

[11] 4,004,591
[45] Jan. 25, 1977

[54] BIRTH CONTROL DEVICE

[76] Inventor: Max G. Freimark, 90870 Ferndale St., Philadelphia, Pa. 19115

[22] Filed: Nov. 17, 1975

[21] Appl. No.: 632,670

[52] U.S. Cl. .............................................. 128/294
[51] Int. Cl.² ........................................ A61F 5/42
[58] Field of Search .................. 128/132 R, 79, 294, 128/138 R, 127

[56] References Cited

UNITED STATES PATENTS

| 3,443,563 | 5/1969 | Ishihama et al. ............... | 128/294 U |
| 3,536,066 | 10/1970 | Ludwig ........................... | 128/132 R |

FOREIGN PATENTS OR APPLICATIONS

| 36,015 | 7/1908 | Austria ............................ | 128/294 |
| 267,218 | 11/1913 | Germany ........................... | 128/294 |
| 210,413 | 9/1909 | Germany ........................... | 128/294 |

*Primary Examiner*—Lawrence W. Trapp
*Attorney, Agent, or Firm*—Nelson E. Kimmelman

[57] ABSTRACT

A prophylactic or contraceptive device made of membraneous material having a generally tubular configuration with a closed end which includes a thicker, reenforced tip. At its open end, there are two flaps extending transversely to the axis of the device with a scalloped intermediate portion. The flaps are maintained in their transverse position by reenforced or thickened edges.

7 Claims, 6 Drawing Figures

U.S. Patent    Jan. 25, 1977    4,004,591
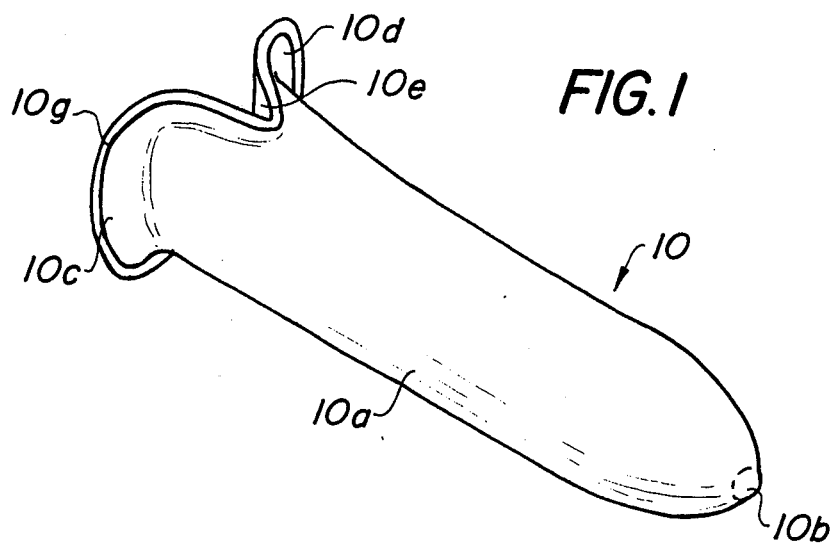
FIG. 1
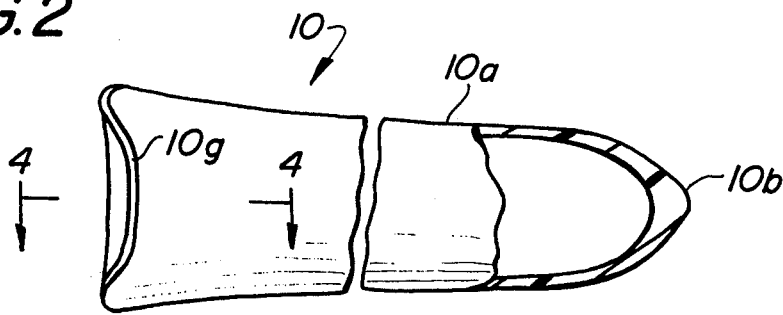
FIG. 2
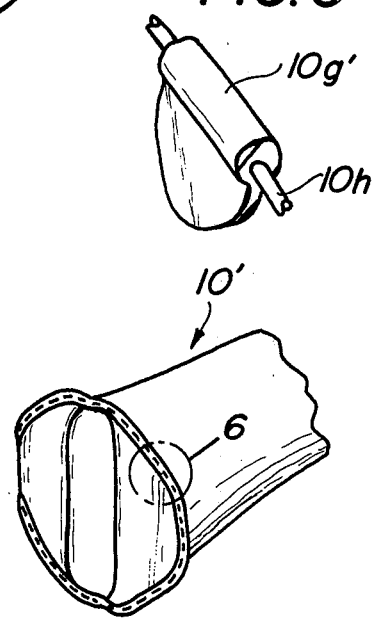
FIG. 6
FIG. 5
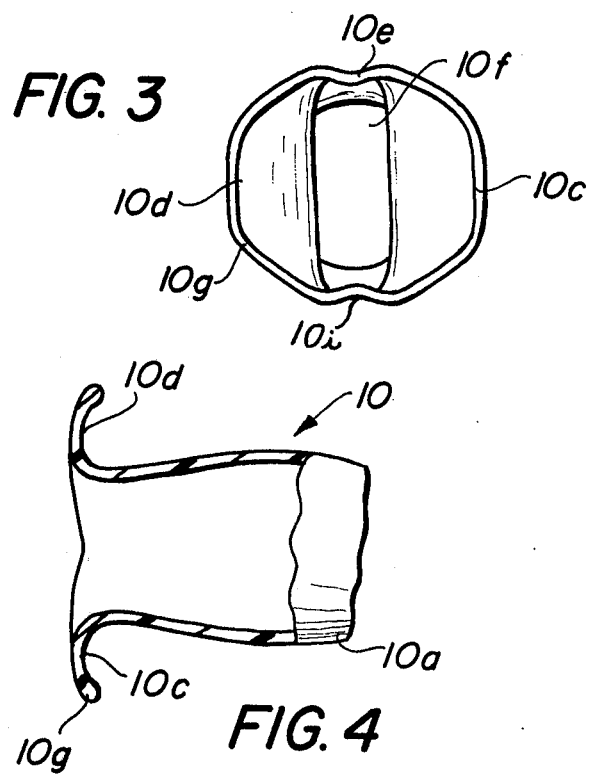
FIG. 3
FIG. 4

BIRTH CONTROL DEVICE

BACKGROUND OF THE INVENTION

1. Field Of The Invention

This invention relates to a prophylactic or birth control device and in particular to such device designed for use by the female partner in coitus.

2. Prior Art

There are, of course, a great number of mechanical types of devices used to prevent conception or the transmission of disease from one to the other partner in coitus. The most well-known include, of course, the IUD, the inter-uterine device which is implanted in the mouth of the uterus. This has been known to cause irritation and other internal difficulties for women and is not as reliable in preventing conception as other types. Besides, it must ordinarily be inserted by a physician or highly trained nurse. Another device is the diaphragm which is generally coated with a spermicide and inserted by the female over the mouth of the uterus. It forms a mechanical as well as a chemical barrier to the entrance of sperm into the uterus. It is subject to being dislodged, is difficult to insert by the woman herself and poses other problems.

There are also prophylactics or sheaths intended to be worn by the male partner made either of strong, fine rubber, or some type of fine animal skin, or some synthetic membrane. Necessarily, in order to provide the desired degree of tactile stimulation to the wearer, it must be quite thin. In general it is elastically fitted on the male organ and during coitus remains stretched and taut, but this taut condition tends to increase the hazard of its being torn or bursting during use. In order to prevent its being dislodged it must fit rather tightly, so that it is bound to cause some physical discomfort to the wearer.

Chemical methods are also employed, the most widely-known being the oral contraceptive known as the "pill" which requires ingestion each day in the interval between the menstrual periods. However, this requires constant diligence on the part of the woman to insure that the pill is taken regularly. Moreover, a number of undesirable side effect have been noted together with the possible potential for longer term serious harm.

It is therefore among the objects of the present invention to provide a prophylactic device that will be effective to provide a mechanical barrier to the unwanted release of sperm into the vaginal cavity. It is another object of the invention to provide a prophylactic device adopted to be worn internally by a woman which is not likely to present the risk of slippage and the consequent risk of conception during use. Still another object is to prevent subjecting the contraceptive to appreciable distention or stretching during the coital act which might result in inadvertent tearing or bursting. Another object is to provide a contraceptive which does not cause discomfort to either party.

SUMMARY OF THE INVENTION

A contraceptive device comprising a generally tubular member made of a membraneous compliant material and having an open end and a closed end, the open end having two flaps extending outwardly and generally transversely to the axis of said device. BRIEF DESCRIPTION OF THE DRAWINGS FIG. 1 is a perspective view of my novel contraceptive apparatus;

FIG. 2 is a fragmentary, partly broken away side elevation view of the device shown in FIG. 1;

FIG. 3 is an end view of the apparatus shown in FIG. 2;

FIG. 4 is a fragmentary sectional view of the device shown in FIG. 2 taken along the section-line 4—4 in the direction indicated;

FIG. 5 is a fragmentary perspective view of still another form of the present invention; and FIG. 6 is an enlarged, partly broken-away view of the circular portion 6 of FIG. 5.

DETAILED DESCRIPTION OF THE DRAWINGS

FIGS. 1–4 show generally at the numeral 10 a novel contraceptive device intended to be worn internally by the female partner according to the present invention. It includes a generally elongated and somewhat tubular portion 10a made of an appropriate material such as thin but strong rubber, plastic or other similar material which is strong enough to withstand the stresses that may be encountered in use. Naturally, it cannot be so thick that it would not transmit the sensation of movement within the vaginal canal.

Its cross-section should be sufficiently large to easily accommodate the average male with an additional clearance space so that the male member will not dislodge it during use. Alternatively, the device may be of several lengths and/or cross-sections to suit the physical dimensions of the partners involved. It has a reinforced or thickened tip 10b and at its open end there are two wings or flaps 10c and 10d. They are disposed substantially transverse to the longitudinal axis and are helped to maintain this position by the reinforced rim 10e which may simply be of the greater thickness than the rest of the device. The rim has a bent or scalloped portion 10e that is shaped to permit exposure of the clitoris during coitus so as not to dull sensation. Additionally, there may be another scalloped portion 10i disposed opposite the portion 10e if desired to enable the device 10 to be put into place in either of two positions and to increase the area of male-female contact. The wings 10c and 10d are designed to cover the labia majora and their substantially transverse position limits the inward movement of the device 10 thereby facilitating its withdrawal when desired.

Another form 10' of the device is shown in FIGS. 5 and 6. This is essentially the same as the device 10 except that the rim or edge 10'g is further reinforced by a relatively rigid wire 10h or equivalent. This helps to maintain the flaps 10c' and 10d' in an outward, transverse position and to prevent undue inward movement of the device 10'.

To use this invention, the device 10 may initially be placed on the male organ prior to intromission or may be inserted into the vaginal canal by hand or any other convenient or appropriate way. The natural curvature of the canal will usually be sufficient to prevent its inadvertent removal. As an added precaution, and to enhance male sensation, the interior of the device should be lubricated so that during coitus there is no undue frictional engagement of the inner surface of the device 10 by the exterior surface of the male organ. Any suitable lubricant may be used such as a mixture of Ortho-Creme with some appropriate face cream in proportions of, say, 33-25%:66-75%. If the device is to be re-used and is made of ordinary rubber or latex, the lubricant should not include oleaginous constituents that may cause the rubber to deteriorate but rather should have water-soluble properties. If the rubber is of the silicone type it is possible to use petroleum jelly or equivalent. If the material of the device is an inexpensive but very strong plastic, the device may be of the single-use type.

Under certain circumstances, it may be also desirable to lubricate the external wall 10a with a spermicidal lubricant of the same type as the inner lubricant except that a water-miscible lubricant may be desired for easier organic absorption.

Also, it may be advantageous prior to use to insert a small amount of an absorbent material such as absorbent cotton, absorbent paper or a sponge at the closed end on the internal wall just opposite the reinforced tip portion 10b. This will tend to prevent inadvertent spillage of seminal fluid when the male organ is withdrawn from the device 10.

Other modifications of the invention, which do not depart from the essence thereof, will occur to one skilled in the art upon perusing the present application and the drawings herein. Therefore, I desire the invention to be limited solely by the claims which follow.

I claim:

1. A contraceptive device to be worn internally by women comprising a generally tubular member made of an integral moisture proof membraneous compliant material and having an open end and a closed end, said tubular member having a cross-section dimensioned to fit snugly within the vaginal canal of the wearer, said cross section being substantially constant from said open end to a region adjacent said closed end, the open end of said tubular member having two flaps normally extending outwardly and generally transversely to the axis of said device, said flaps being contoured to cover the labia majora of the wearer and the epidermal area adjacent thereto.

2. The device according to claim 1 wherein said open end also includes at least one scalloped edge portion.

3. The device according to claim 2 wherein there are at least two of said scalloped portions disposed generally opposite one another on the edge of said open end.

4. The device according to claim 1 wherein said closed end is reenforced by having a wall thickness greater than the side walls of said device.

5. The device according to claim 1 wherein the edges of said open end are reenforced by having a thickness greater than the side walls of said device.

6. The device according to claim 1 wherein the edges of said open end are reenforced by a relatively rigid elongated member formed within said edge.

7. The device according to claim 2 wherein said scalloped portion is shaped and dimensioned to expose the clitoris of the wearer during use.

* * * * *